(12) United States Patent
Munk et al.

(10) Patent No.: US 11,127,487 B2
(45) Date of Patent: Sep. 21, 2021

(54) SYSTEMS AND METHODS FOR CYBER-ENABLED STRUCTURE ELUCIDATION

(71) Applicants: Morton Munk, Tempe, AZ (US); Klaus-Peter Schulz, Tempe, AZ (US)

(72) Inventors: Morton Munk, Tempe, AZ (US); Klaus-Peter Schulz, Tempe, AZ (US)

(73) Assignee: Arizona Board of Regents on Behalf of Arizona State University, Tempe, AZ (US)

( * ) Notice: Subject to any disclaimer, the term of this patent is extended or adjusted under 35 U.S.C. 154(b) by 332 days.

(21) Appl. No.: 16/268,232

(22) Filed: Feb. 5, 2019

(65) Prior Publication Data

US 2019/0318808 A1    Oct. 17, 2019

Related U.S. Application Data

(60) Provisional application No. 62/656,543, filed on Apr. 12, 2018.

(51) Int. Cl.
*G16C 20/20* (2019.01)

(52) U.S. Cl.
CPC .................................. *G16C 20/20* (2019.02)

(58) Field of Classification Search
None
See application file for complete search history.

(56) References Cited

U.S. PATENT DOCUMENTS

2002/0173920 A1* 11/2002 Xu .................. G01N 24/08
702/27

OTHER PUBLICATIONS

Of Brown et al. ("Hyperstructure model for chemical structure handling: generation and atom-by-atom searching of hyperstructures" J Chem Inf Comput Sci. 1992 32 (5), 522-531) (Year: 1992).*
Elyashberg, et al., Contemporary Computer-Assisted Approaches to Molecular Structure Elucidation; RSC Publishing: Cambridge, UK, 2012.
Schaller, et al., Software Development in Chemistry, Gesellschaft Deutscher Chemiker, vol. 3, R. Moll (Ed.), Frankfurt, Germany, 1995.
Badertscher, et al., "ASSEMBLE2: A Structure Generator." Chemometrics and Intelligent Laboratory Systems, 51, 73-79 (2000).
Batbayar, et al., Norditerpinoid Alkaloids from Delpinium Species. Phytochem. 2002, 62, 543-550.
Branco, et al., Two Monoisoprenylated Flavonoids from Vellozia Graminifolia. Phytochem. 1998, 47, 471-474.
Christie, et al., "Structure Generation by Reduction: A New Strategy for Computer-Assisted Structure Elucidation," J. Chem. Inf. Comput. Sci., 28, 87-93 (1988).
Christie, et al., "The Application of Two-Dimensional Nuclear Magnetic Resonance Spectroscopy in Computer-Assisted Structure Elucidation," Anal. Chim. Acta, 200, 347-361 (1987).
Christie, et al., "The Role of Two-Dimensional Nuclear Magnetic Resonance Spectroscopy in Computer-Enhanced Structure Elucidation," J. Am. Chem. Soc., 113, 3750-3757 (1991).

(Continued)

*Primary Examiner* — Roy Y Yi
(74) *Attorney, Agent, or Firm* — Polsinelli PC

(57) ABSTRACT

Various embodiments for system and methods for cyber-enabled structure elucidation are disclosed.

7 Claims, 3 Drawing Sheets

(56) References Cited

OTHER PUBLICATIONS

Cyber-Based Structure Elucidation, Introduction to Cheminformatics, Harry Stewart Talks, 2010, [online] https://hstalks.com/t/2022/cyber-based-structure-elucidation/.
Deb, Multi-Objective Optimization using Evolutionary Algorithms, Wiley: Chichester, 2001, p. 28.
Dolak, et al., "Structure of U-54702 Using Computer-Assisted Structure Elucidation," Current Chemotherapy and Infectious Disease, J. D. Nelson and C. Grassi (editors), American Society for Microbiology, 1, 467-469 (1980).
Falcone, et al., "The Rearrangement of 2-Carbomethyoxy-2-Phenylselenocyclohexanone," Synthetic Communications, 9(8), 719-726 (1979).
Fotso, et al., "Bhimamycin A-E and Bhimanone: Isolation, Structure Elucidation and Biological Activity of Novel Quinone Antibiotics from a Terrestrial Streptomycete," J. Antibiotics, 56, 931-941 (2003).
Jaspars, Computer Assisted Structure Elucidation of Natural Products Using Two-dimensional NMR Spectroscopy. Nat. Prod. Rep., 1999, 16, 241-248.
Korytko, et al., "Houdini: A New Approach to Computer-Based Structure Generation," J. Chem. Inf. Comput. Sci., 43, 1434-1446 (2003).
Lipkus, et al., "A Manipulation of Two-Dimensional NMR Spectra Based on Graph Theory," J. Magn. Reson., 102, 24-28 (1993).
Lipkus, et al., "Automated Classification of Candidate Structures for Computer-Assisted Structure Elucidation," J. Chem. Inf. Comput. Sci., 28, 9-18 (1988).
Lipkus, et al., "Combinatorial Problems in Computer-Assisted Structural Interpretation of Carbon-13 NMR Spectra," J. Chem. Inf. Comput. Sci., 25, 38-45 (1985).
Liu, et al., "Computational Techniques for Vertex Partitioning of Graphs," J. Chem. Inf. Comput. Sci., 30, 263-269 (1990).
Liu, et al., "Computer-Assisted Graph-Theoretical Construction of 13C NMR Signal and Intensity Patterns," J. Magn. Reson., 87, 457-474 (1990).
Munk, "Computer-Based Structure Determination: Then and Now," J. Chem. Inf. Comput. Sci., 38, 997-1009 (1998).
Munk, et al., "Chemical Information Processing in Structure Elucidation," Recent Advances in Chemical Information II, H. Collier, editor, Royal Society of Chemistry, Cambridge, U.K. 247-263 (1993).
Munk, et al., "Computer-Assisted Chemical Structure Analysis," Mikrochim. Acta, II, 199-215 (1986).
Munk, et al., "Computer-Assisted Structure Elucidation," Fresenius Z. Anal. Chem., 313, 473-479 (1982).
Munk, et al., "Computer-Based Structure Determination," The Encyclopedia of Computational Chemistry, P.v R Schleyer, N. L. Allinger, T. Clark, J. Gasteiger, P. A. Kolllman, H. F. Schaefer III, P. R. Schreiner, (Eds.); John Wiley and Sons, Chichester, 1998, pp. 2785-2811.
Munk, et al., "Computer-Mediated Reduction of Spectral Properties to Molecular Structures. General Design and Structural Building Blocks," Anal. Chim. Acta, 184, 1-19 (1986).
Munk, et al., "Stereoisomer Generation in Computer-Enhanced Structure Elucidation," J. Chem. Inf. Comput. Sci., 33, 812-825 (1993).
Munk, et al., "The Characterization of Structure by Computer," Anal. Chim. Acta, 216, 57-68 (1989).
Munk, et al., "The Neural Network as a Tool for Multispectral Interpretation," J. Chem. Inf. and Comput. Sci., 36, 2, 231-238 (1996).
Munk, et al., "The Role of NMR Spectra in Computer-Enhanced Structure Elucidation," Computer-Enhanced Analytical Spectroscopy, Chap. 5, vol. 3, P. Jurs, editor, Plenum, New York (1992).
Munk, et al., Structure Determination via Computer-Based Spectrum Interpretation. The Encyclopedia of Computational Chemistry, Schleyer, P. v. R.; Allinger, N. L.; Clark, T.; Gasteiger, J.; Kollman, P.A.; Schaefer III, H. F.; Schreiner, P. R., Eds., Wiley: Chichester, 1998. pp. 2785-2811.
Munk, et al., The Structure of Actinobolin, J. Amer. Chem. Soc., 1968, 90, 1087-1089.
Nair, Alkaloids from Nerine filifolia. Phytochem. 2005, 66, 373-382.
Penchev, et al., "INFERCNMR: A 13C NMR Interpretive Library Search System," J. Chem. Inf. Model., 2012, 52, 1513-1528.
Pretsch, et al., "C13 Shift: A Computer Program for the Prediction of 13c NMR Spectra Based on an Open Set of Additivity Rules," J. Chem. Inf. Comput. Sci., 32, 291-295 (1992).
Razinger, et al., "Graph Automorphism Preception Algorithms in Computer-Enhanced Structure Elucidation," J. Chem. Inf. Comput. Sci., 33, 197-201 (1993).
Robb, et al., "A Neural Network Approach to Infrared Spectrum Interpretation," Mikrochimica Acta, I, 131-155 (1990).
Robb, et al., "Neural Network Models for Infrared Spectrum Interpretation," Mikrochim. Acta, II, 505-514 (1991).
Schaller, et al., "Spectra Estimation for Computer-Aided Structure Determination," J. Chem. Inf. Comput. Sci., 36, 2, 239-243 (1996).
Schulz, et al., "Applications of a HOUDINI-based Structure Elucidation System," J. Chem. Inf. Comput. Sci., 43, 1447-1456 (2003).
Shelley, et al., "A Unique Computer Representation for Molecular Structures," Anal. Chim. Acta/Computer Techniques and Optimization, 103, 245-251 (1978).
Shelley, et al., "An Approach to Automated Partial Structure Expansion," Anal. Chim. Acta/Computer Techniques and Optimization, 103, 121-132 (1978).
Shelley, et al., "An Approach to the Assignment of Canonical Connection Tables and Topological Symmetry Perception," J Chem. Inf. Comput. Sci., 19, 247-250 (1979).
Shelley, et al., "CASE, A Computer Model of the Structure Elucidation Process," Anal. Chim. Acta/Computer Techniques and Optimization, 133, 507-516 (1981).
Shelley, et al., "Computer Perception of Topological Symmetry," J. Chem. Inf. Comput. Sci., 17, 110-113 (1977).
Shelley, et al., Computer Prediction of Substructures from Carbon-13 Nuclear Magnetic Resonance Spectra, Anal. Chem., 54, 516-521 (1982).
Shelley, et al., Computer-Assisted Structure Elucidation, Current Chemotherapy and Infectious Disease, J. D. Nelson, C. Grassi (editors), American Society for Microbiology, 1, 55-56 (1980).
Shelley, et al., "Interactive Structure Elucidation," A.C.S. Symposium Series, No. 54, Computer-Assisted Structure Elucidation, 1977, pp. 92-107.
Shelley, et al., "Signal Number Prediction in Carbon-13 Nuclear Magnetic Resonance Spectrometry," Anal. Chem., 50, (1978). 1522-1527.
Steinbeck, Recent Developments in Automated Structure Elucidation of Natural Products. Nat. Prod. Rep. 2004, 21, 512-518.
Steinbeck, SENECA: A Platform-Independent, Distributed,and Parallel System for Computer-Assisted Structure Elucidation in Organic Chemistry, J. Chem Inf. Comput. Sci 2001, 41, 1500-1507.
Trulson, et al., "Table-Driven Procedure for Infrared Spectrum Interpretation," Anal. Chem., 55, 2137-2142 (1983).
Wasserman, et al., "Synthesis and Characterization of Pyrrolinecarboxylates Formed by the Reaction of Vicinal Tricarbonyl Derivatives with Aldehyde Schiff Bases," Heterocycles, 35, 975-994 (1993).
Woodruff, et al., "A Computerized Infrared Spectral Interpreter as a Tool in Structure Elucidation of Natural Products," J. Org. Chem., 42, 1761-1767 (1977).
Woodruff, et al., "Computer Assisted Infrared Spectral Interpretation," Research/Development, 28, 34-38 (1977).
Woodruff, et al., "Computer-Assisted Interpretation of Carbon-13 Nuclear Magnetic Resonance Spectra: Application to Structure Elucidation of Natural Products," Anal. Chem., 49, 2075-2080 (1977).
Woodruff, et al., "Computer-Assisted Interpretation of Infrared Spectra," Anal. Chim. Acta/Computer Techniques and Optimization, 1, 13-23 (1977).
Zupan, et al., "Hierarchical Clustering," Vestn. Slov. Kem. Drus., 30, 61-76 (1983).

(56) References Cited

OTHER PUBLICATIONS

Zupan, et al., "Hierarchical Tree Based Storage, Retrieval and Interpretation of Infrared Spectra," Anal. Chem., 57, 1609-1616 (1985).

Zupan, et al., "The Feed-Back Search of Hierarchical Trees," Anal. Chem., 58, 3219-3225 (1986).

* cited by examiner

SYSTEMS AND METHODS FOR CYBER-ENABLED STRUCTURE ELUCIDATION

CROSS REFERENCE TO RELATED APPLICATIONS

This is a non-provisional application that claims benefit to U.S. Provisional Application Ser. No. 62/626,543; filed on Feb. 5, 2018, which is herein incorporated by reference in its entirety.

FIELD

The present disclosure generally relates to structure elucidation, and in particular to systems and methods for cyber-enabled structure elucidation.

BACKGROUND

In the search for new chemotherapeutic agents, natural products continue to be an important source. An important step in the process leading to the development of a proven drug is the elucidation of the chemical structure of the active principle isolated from the extract of the plant or animal source. Structure elucidation has traditionally been the responsibility of chemists experienced in the task. Beginning around fifty years ago some chemists began to explore the advantages of computational techniques—mainly artificial intelligence, a term used here in its broadest sense—in augmenting productivity in solving structure elucidation problems. In recent years, significant advances in the development of practical computer software for the elucidation of structure have been reported and efforts to further improve performance continue unabated.

It is with these observations in mind, among others, that various aspects of the present disclosure were conceived and developed.

BRIEF DESCRIPTION OF THE DRAWINGS

Corresponding reference characters indicate corresponding elements among the view of the drawings. The headings used in the figures do not limit the scope of the claims.

DETAILED DESCRIPTION

Introduction

Figure 1:
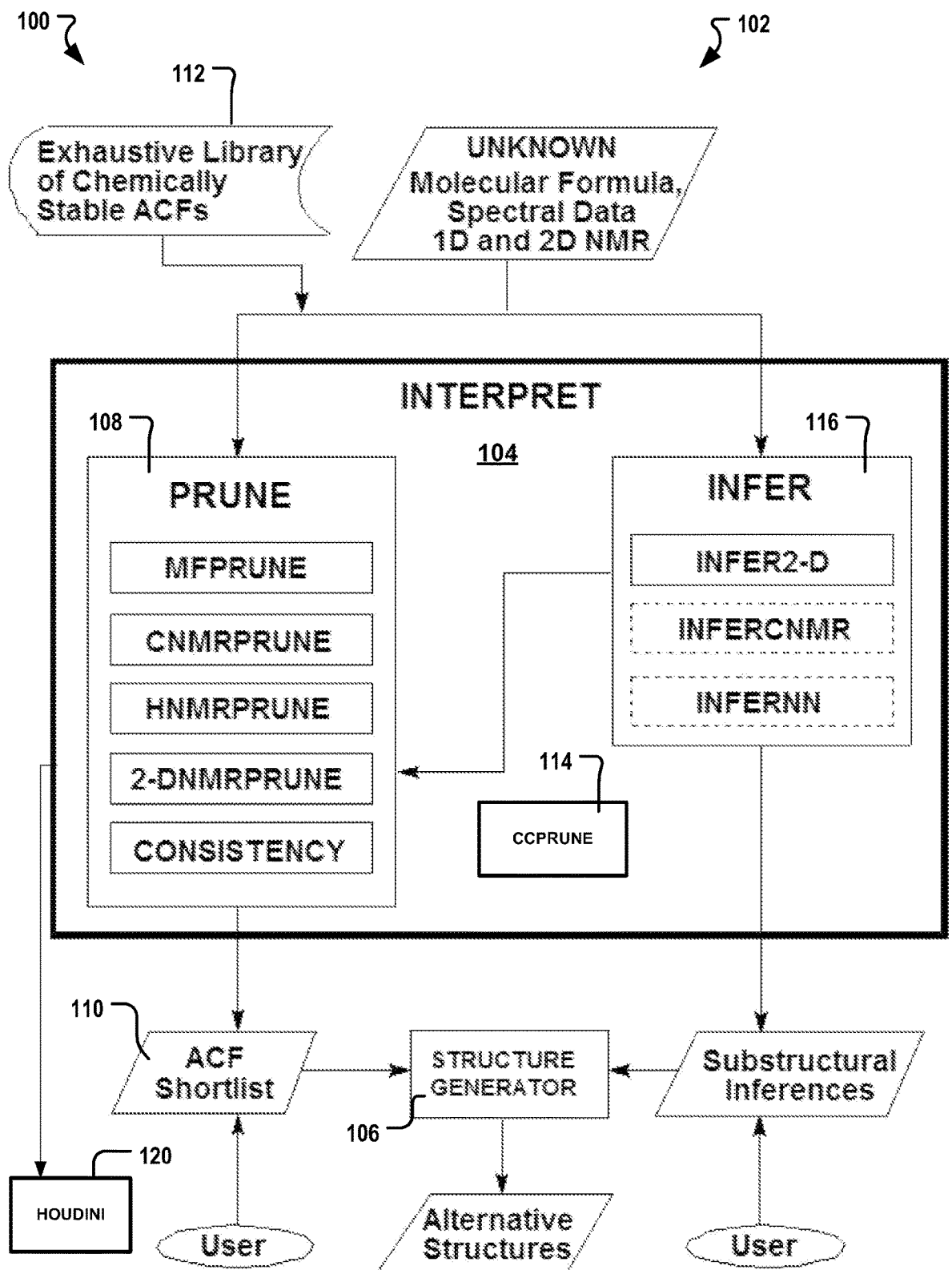
FIG. 1 is a flow chart showing the operations of one embodiment of a structure elucidation system, according to aspects of the present disclosure.

Why is structure elucidation important? It has application in chemistry and related fields, but it is especially important in the pharmaceutical industry since many of the best drugs are complex, carbon-based compounds derived from natural sources, both plant and animal. Structure elucidation is a necessary step in the process of bringing such a drug to market. Consider TAXOL®, a promising cancer drug. It is a naturally occurring, high molecular weight, complex compound ($C_{47}H_{51}NO_{14}$) that was first isolated from the yew tree, which is native to Canada and the northwest United States. The compound is present in only very small amounts in the bark and the demand for it cannot, and should not, be met by stripping the bark of all yew trees. A more available and cost effective source is required: synthesis, that is, manufacturing the drug. However, a detailed knowledge of the chemical structure is required in order to develop such a process: structure elucidation must precede synthesis. The chemical structure is also a factor in patent protection.

Structure elucidation can be expressed as an equation:

$$\text{Structure}=f(\text{Properties}) \quad [1]$$

Structure is a function of properties. Today, the properties that form the basis of cyber-enabled structure elucidation are the spectroscopic properties of the compound of unknown structure. Carbon and hydrogen nuclear magnetic resonance in particular are especially powerful tools in deducing the carbon skeleton of a complex compound. The function $f$ is not a mathematical equation; rather it is a set of logical steps. The goal of the present novel concept described herein is to elaborate the function fin the form of a computer program. That is an ambitious goal: a computer program that simulates the high level of specialized human intelligence required to treat a large and complex problem domain. Early in the work in this area, it became evident that a strict expert system, which attempts to mimic step-by-step what is done by the chemist, is not applicable because in the hands of the chemist the process is filled with intuitional leaps. Currently, intuitional leaps are not readily amenable to computer modeling. Thus, for computer implementation, an entirely different approach is needed, one that leads to the same end result, only faster and more reliably. Therein lies the challenge, and there is no one satisfactory approach to this technical problem as evidenced by the diverse methods described by workers in the field.

There are four capabilities of importance in cyber-based structure elucidation: spectrum interpretation, structure generation, spectrum prediction, and spectrum comparison. Spectrum interpretation is the process by which spectral data are reduced to structural inferences that are usually expressed as substructures predicted to be present or absent in the compound under study. Structure generation serves to generate complete molecular structures compatible with these structural inferences. Spectrum prediction is the process by which the spectral properties of a compound are predicted from its molecular structure (the reverse of the equation [1] above). Spectrum comparison serves to identify the goodness of the fit between predicted and observed spectra. The implementation of these capabilities in effective ways can provide a framework upon which a comprehensive cyber-enabled system of structure elucidation can be built.

SESAMI System: Characteristics

Referring to FIG. 1, a SESAMI system 100 of the present disclosure, defining at least one application 102 comprising a plurality of subsystems, services, and/or modules as further described herein, is built on a platform of just two of the above capabilities: spectrum interpretation and structure generation. Using these two capabilities, the SESAMI system 100 is capable of directly reducing the collective spectral properties of an unknown compound to, preferably, a single structure, but no more than a very small number of compatible structures. In such a two-capability system, spectrum interpretation plays a demanding role: it must be capable of producing a set of substructural inferences sufficiently rich in information content to dramatically narrow the number of compatible molecular structures, again, preferably to one. However, it should be noted that even a small set of alternative structures is a useful outcome because experienced chemists are proficient at readily and rapidly identifying the correct structure among a small set of alternatives. If additional information is required to narrow the number of compatible molecular structures, the output of the SESAMI system 100 provides invaluable guidance in the design of the necessary experiments. The SESAMI system 100 includes non-exhaustive attributes considered to be important in designing a system that is as efficient as it is useful.

Given the enormous structural diversity of compounds found in nature, in some embodiments, the SESAMI system 100 is capable of producing the entire range of structures compatible with the observed spectral data, without exception. Further, embodiments of the SESAMI system 100 are not limited to certain types of structures or the contents of one or more databases. In short, the SESAMI system 100 may be exhaustive in scope. The goal is to assure the user that other than the compounds generated by the program, there are no additional structures equally consistent with the collective spectral data; that no equally compatible structure has been overlooked. Thus, the SESAMI system 100 may employ a deterministic approach and not a stochastic approach. A stochastic approach to structure elucidation neither guarantees a solution that is exhaustive, nor one that includes the correct structure.

In some embodiments, it is critical that structural inferences are used prospectively, as early in the structure generation process as possible, in order to produce a timely result (that is, a result as close to a conversational time frame as possible) and avoid combinatorial explosion.

Spectral data may give rise to ambiguous inferences or alternative inferences. Such information must be used efficiently, that is, directly without preprocessing. Further, the process may operate in either fully automated or interactive mode.

SESAMI System: Methodology: Spectrum Interpretation

FIG. 1 is a simplified flow diagram of the overall SESAMI system 100. The SESAMI SYSTEM 100 may include one or more of an application 102 or program, defining major subsystems, such as the INTERPRET subsystem 104 and the STRUCTURE GENERATOR 106 subsystem shown as rectangular boxes. The INTERPRET subsystem 104 displays the component procedures, each of which is a separate subsystem seamlessly joined to all of the other subsystems.

The INTERPRET subsystem 104 may define a two-track spectrum interpretation program. On one track, the molecular formula and collective spectral properties of the unknown are processed by a PRUNE subsystem 108 to give rise to an atom-centered component (ACF) Shortlist 110, a set of small, uniformly sized, explicitly-defined "basic units of structure" each of which is compatible with the observed collective spectral data. An ACF is an atom-centered fragment with one concentric layer of nearest neighbors and two layers of bonds (for example, a methylene centered ACF: =CH—CH$_2$—O—). The central atom of the ACF is always valence satisfied, but at least one first layer atom has residual valence. The PRUNE subsystem 108 produces the ACF Shortlist 110 by acting on an exhaustive library of ACFs 112 (stored within a database or otherwise digitally stored or accessible), each of which is assigned a set of spectral properties. Those properties may include $^1$H and $^{13}$C-NMR data. In some embodiments, the exhaustive ACF library 112 defines the entire domain of compounds that can be generated by the SESAMI system 100, and includes ACFs derived from elements carbon, hydrogen, oxygen, nitrogen, all of the halogens and sulfur (to a limited extent), the elements most commonly found in naturally occurring compounds, a major focus of the SESAMI system 100. (The SESAMI system 100 is not limited to these elements. The application 102 defined by the SESAMI SYSTEM 100 is designed accept additional elements to enlarge the domain of compounds treated.)

The PRUNE subsystem 108 is modular in nature and consists of programs designed to act as constraints. During execution of the application 102, the PRUNE subsystem 108 is operable to delete or temporarily remove an ACF from the exhaustive library of ACFs 112 if its elemental composition is incompatible with the molecular formula of an unknown compound (MFPRUNR), if its assigned spectral properties are incompatible with either the observed one-dimensional $^1$H or $^{13}$C-NMR spectral data (HNMRPRUNE, CNMRPRUNE), or if its structure is incompatible with the 2D NMR data (2-DNMRPRUNE). The surviving ACFs are then subjected to an internal consistency check (CONSISTENCY) giving rise to or otherwise outputting the ACF Shortlist 110. The ACF Shortlist 110 may be organized into subsets, one subset for each non-hydrogen atom in the unknown. The subset of ACFs for each non-hydrogen atom contains only those ACFs that represent a plausible immediate structural environment for that non-hydrogen atom. The subset for each carbon atom is assigned its associated $^{13}$C-NMR chemical shift.

If the PRUNE subsystem 108 operated perfectly, the subset of ACFs for each non-hydrogen atom would contain only a single ACF, the one that is actually present in the structure of the unknown. However, the ACF is too small a fragment to permit a distinction to be made between each and every ACF solely on the basis of spectral properties. Thus, in practice, each subset usually contains more than one ACF, only one of which is correct. Although each ACF subset does therefore contain invalid information, that is not a problem. However, if the correct ACF is missing from one or more ACF subsets, that is a serious problem because the correct molecular structure cannot be built. Thus, the PRUNE subsystem 108 may be biased toward retaining an invalid ACF rather than eliminating a valid one.

In some embodiments, the PRUNE subsystem 108 may include a module, subsystem, or service called CCPRUNE 114, which serves to further constrain the number of surviving ACFs. This is especially important in in the case of higher molecular weight compounds where a large number of invalid ACFs can degrade execution efficiency. In addition to the earlier described constraints, ACFs could be distinguishable from one another utilizing the spectral-coupling between hydrogens on adjacent carbon atoms of the ACF, information that is readily available from the $^1$H NMR spectrum. CCPRUNE 114 examines the structure of each ACF in each ACF subset for compatibility with observed proton coupling constants. The ACF is a small structural unit. As a consequence, the pruning ability of CCPRUNE 114 is limited, however, as problem-solving has demonstrated, the positive impact in constraining the number of molecular structures generated can be significant in some cases. In its operation, CCPRUNE 114 examines the coupling(s) associated with the hydrogen(s) on the central carbon atom of each ACF in each carbon-centered ACF subset. (Note that the central carbon atom may be —CH<, —CH=, —CH$_2$—, CH$_2$= or CH$_3$—.) Thus, CCPRUNE 114 requires information from the heteronuclear two-dimensional $^1$H, $^{13}$C chemical shift correlation (HSQC) to correctly identify the hydrogen atoms (and therefore their corresponding proton signals) attached to the central carbon atom of an ACF. Recall that the chemical shift of the central carbon atom of each ACF in a given ACF subset is the same, as is the number of attached hydrogen atoms. Other structural features of the ACFs in a subset may differ, even significantly (for example, the nature of first-layer atoms, or hybridization of the central carbon atom). The observed proton coupling data provide information on the presence or absence of vicinal hydrogen atoms, that is, the presence or absence of first-layer hydrogen bearing carbon atoms. (Consideration of coupling involving first-layer hydrogens on atoms other than carbon is optional currently.)

The knowledge base of CCPRUNE 114 includes the known proton coupling constant differences between vicinal and long-range coupling. Values for the latter are less than those of the former. Consider an ACF in a given ACF subset which bears a single hydrogen atom on the central carbon atom and two hydrogen atoms on a first layer carbon atom. CCPRUNE 114 prunes that ACF from that subset of ACFs if the observed proton coupling constants for the hydrogen on the central carbon atom are less than the upper limit assigned to long-range coupling. In effect, if all observed proton coupling constants for central carbon hydrogen atoms are less than this threshold, only long range coupling is indicated and therefore any ACF bearing vicinal hydrogen atoms is invalid and pruned from the ACF subset (described below for additional clarification).

Depending on ACF's structural features, three different upper thresholds are assigned to long-range coupling. In considering an ACF (a) bearing hydrogen atoms on adjacent sp3 carbon atoms, the upper threshold is set at 2.0 Hz.; (b) where one hydrogen atom is attached to an sp2 carbon atom, the other to an adjacent sp3 or sp2 carbon atom, the threshold is set lower, at 1.5 Hz.; and (c) involving a —CH= as a first-layer group in cases where it is possible that an aldehyde is present in the unknown, the threshold is set to 0.7 Hz. Thresholds (b) and (c) include systems in which an sp2 carbon atom is joined to an sp3 carbon atom. The difference in assigned threshold values is based on the observation that the vicinal coupling constant for >CH—CH=A is less when A is oxygen than when A is carbon. For example, consider a case where an aldehyde function is known or suspected to be present in the unknown compound. To determine the validity of the ACF —CH2-CH2-CH=, the coupling constant threshold of 0.7 Hz rather than 1.5 Hz. would be applied and that ACF would be deleted only if all vicinal coupling constants associated with central carbon hydrogens are less than 0.7 Hz. In practice, if all observed proton coupling constants are less than 0.7 Hz., every ACF in the particular ACF subset which possesses vicinally-related hydrogen atoms would be deleted. The user can change the described default values for the coupling constant thresholds.

CCPRUNE 114 only acts on ACFs where either the central carbon atom or the first layer carbon atom bears at least two hydrogens. Consider the case of single hydrogen atoms on adjacent sp3 carbon atoms. Although the usual range for such coupling is 6 to 7 Hz, it can be considerably less. In rigid systems where both connected carbon atoms are sp3 hybridized, that is, >CH—CH<, the vicinal coupling constant is highly dependent on the dihedral angle between the C—H bonds and can approach 0 Hz. Thus, the vicinal coupling constant in a valid ACF such as >CH—CH(—OCH$_3$)—C (that is, an ACF with only one pair of vicinal hydrogens) could be less than 2.0 Hz if part of a rigid system. In such a case, a valid ACF would be deleted, leading to the omission of the correct molecular structure. However, in an ACF as >CH—CH$_2$—OCH$_3$, at least one of the two possible vicinal hydrogen pairs would be expected to have a more usual coupling constant, i.e., above 2.0 Hz.

It should be noted that threshold values in CCPRUNE 114 are set low. Consequently, invalid ACFs may be retained in an ACF subset (false positives). As indicated earlier, it is better to retain an invalid ACF, which does not compromise the solution, than to exclude a valid ACF. As an example, large (>5 Hz) long-range coupling constants have been occasionally observed. In the case of a compound with such an observed coupling, the program could falsely identify (and retain) an invalid ACF as meeting the vicinal hydrogen relationship.

Systems in which the two hydrogens atoms attached to a central sp3 carbon atom reside in different chemical environments can give rise to two distinct proton signals. Such geminal hydrogen atoms can couple giving rise to a characteristically high coupling constant, 10 Hz or above. Cases where geminal hydrogens give rise to two signals are treated as a special case. They reveal their presence by a coupling constant Hz. In determining whether an ACF should be retained or deleted, the geminal coupling is ignored and the remaining coupling constants, related to vicinal coupling, are evaluated based on structural considerations utilizing the three thresholds described above.

The second track of INTERPRET 104 is the INFER subsystem 116. The INFER subsystem 116, like the PRUNE subsystem 108, may be modular in nature and consist of separate programs, the output of each of which is one or more structural inferences expressed as substructures predicted to be present in the unknown. However, in contrast to the small, explicitly defined, uniformly-structured ACF produced by the PRUNE subsystem 108, the substructures produced by the INFER subsystem 116 can be of any size, complexity, ambiguity (that is, they need not be explicitly defined in terms of atoms or bonds) and degree of overlap with other substructures. A given inference may also consist of two or more alternative substructures, only one of which is valid. The INFER subsystem 116 may include two programs: INFER2D and INFERCNMR. INFERNN, a neural network based program, may also be included.

Two-dimensional nuclear magnetic resonance (NMR) is a powerful probe of the nature of the carbon skeleton of the unknown. INFER2D can accept the output of all of the through-bond atom correlations produced by 2D NMR procedures and build substructures based on the information. The heteronuclear single quantum correlation (HSQC) experiment reveals one-bond carbon-hydrogen correlations. COSY typically describes three-bond hydrogen-hydrogen correlations, that is, vicinally-related hydrogen atoms. The long-range COrrelation SpectroscopY (COSY) experiment can reveal four and five-bond H—H correlations. The Heteronuclear Multiple Bond Correlation (HMBC) experiement typically identifies long-range carbon-hydrogen correlations that do not distinguish between two and three intervening bonds. However, four-bond correlations, although less common, are known. The 2D-INADEQUATE experiment reveals one-bond carbon-carbon correlations.

INFER2D of the INFER subsytem 116 performs the following tasks:
1. INFER2D generates structural units of two connected carbon atoms from COSY and HSQC data. COSY identifies vicinally related hydrogen atoms. Therefore, the carbon atoms to which those hydrogens are attached must be joined together. The HSQC data identifies those chemical shift labeled carbon atoms.

2. INFER2D generates structural units of two connected carbon atoms directly from the one-bond carbon-carbon correlations obtained from the 2D INADEQUATE experiment.

3. The HMBC experiment correlates a chemical shift-labeled carbon atom and a chemical shift labeled-hydrogen atom that are separated by two or three bonds (sometimes by four bonds). Since HSQC data identifies the carbon atom attached to a hydrogen atom, HMBC generates structural inferences requiring two chemical shift labeled carbon atoms to be either directly connected to one another or separated by one other non-hydrogen atom. In the case of the four-bond correlation, the separation is by two non-hydrogen atoms. The inference here then is a set of two or three alternative inferences.

4. INFER2D attempts to build larger substructures using several different series of logical steps, the simplest of which is appropriately combining smaller substructures containing the same chemical-shift labeled carbon atom.

It should be noted that only connectivity, not bond type, is assigned by INFER2D.

INFERCNMR is a $^{13}$C-NMR interpretive library search system. The function of the program is to retrieve substructures from the reference compounds of a library of assigned $^{13}$C-NMR spectra which are predicted to be present in the unknown. In an assigned reference library, both the spectrum and molecular structure of each entry are present and each carbon atom is assigned its chemical shift. INFERCNMR was developed with a specific purpose in mind; to complement, not duplicate, the information provided by INFER2D, although admittedly that is not always the case, that is, the structural inferences can at times merely overlap. INFER2D requires both $^1$H NMR and $^{13}$C-NMR information. The richer the hydrogen content of the compound under study, the better the chance INFER2D can provide useful structural information. Compounds with low hydrogen content, for example aromatic compounds, may only provide limited and insufficient information to narrow the output of compatible molecular structures to a small number. INFERCNMR is not limited by hydrogen content and there are cases where the additional substructural information provided by INFERCNMR is crucial to a satisfactory solution of the problem.

At its core, INFERCNMR is a subspectrum matching program. Any subset of the signals of a $^{13}$C-NMR spectrum can be considered to be a subspectrum. However, if the signals of the subspectrum correspond to a single unit of connected carbon atoms, then we have a substructure. The premise implicit in INFERCNMR is that if an unknown and a reference library compound have a subspectrum in common, and if the subspectrum of the reference compound corresponds to a single unit of connected carbon atoms, that is, to a substructure, then that substructure is also present in the unknown. From the premise it can be seen that INFERCNMR is not limited to pre-defined substructures. Any substructure contained in a reference compound in the library can, in principle, be retrieved. However, INFERCNMR is database dependent. It is not possible to predict a substructure which is not present in a reference compounds of the library. Thus, a generally useful interpretive library search system requires a reference library of great structural diversity. An important characteristic of the interpretive library search is that there need not be overall structural similarity between a reference compound and the unknown in order to retrieve a substructure common to both.

INFERCNMR input consists of two kinds of information: the chemical shift of each carbon signal in the spectrum and its multiplicity; and the molecular formula of the unknown. The output of INFERCNMR is one or more explicitly defined substructures retrieved from the reference compound library. Heteroatoms attached directly to the carbon atoms of a retrieved substructure are considered to be part of the predicted substructure. An estimated prediction accuracy is assigned to each substructure. Handing a predicted substructure to the structure generator says that substructure must be present in the unknown. If the predicted substructure is invalid, that is, a false positive, every generated molecular structure will be incorrect. Thus, only substructures with a high prediction accuracy should be utilized. INFERCNMR also assigns a chemical shift from the observed spectrum to each carbon atom of the predicted substructure. Where there is ambiguity in assignment, a set of alternative chemical shifts are assigned to those carbon atoms of the substructure.

The integration of INFERCNMR in the SESAMI system 100 is unique in one sense. Other program components in the SESAMI system 100 are designed to allow for, but do not require, user involvement. INFERCNMR does require user involvement in processing the substructural information generated by the program. The output of INFERCNMR is a visual set of substructures each of which is highlighted and embedded in the reference compound of the library from which it was retrieved. A predicted reliability is assigned to each substructure. The user decides the minimum acceptable reliability. Generally, the minimum acceptable reliability is 90%, but the user can set a narrower reliability range, for example, 95%. The visual output is examined by the user and the substructure (or substructures) to be handed to the structure generator is determined on the basis of substructure reliability and chemical intuition. A combination of two substructures with little overlapping structural information can be far more effective in limiting the number of candidates structures output by the SESAMI system.

SESAMI System: Methodology: Structure Generation

A highly efficient structure generator is essential in a comprehensive cyber-enabled structure elucidation system designed to treat complex, high molecular weight compounds of carbon. Such efficiency depends in large measure on the ability to prospectively utilize the information contained in the structural inferences produced by the spectrum interpretation program referred to as INTERPRET 104. The goal is to identify invalid molecular structures well before they are generated, at the earliest possible stage. The result is the exclusion of many large families of invalid molecular structures early in the structure generating process, thereby eliminating the need for a substantial amount of fruitless computational time. The "earlier-the-better" was the mantra of the current development. Such efficiencies are absolutely essential if the solution of complex, high molecular weight chemical compounds is to be achieved in a "conversational" fashion. In some embodiments, the SESAMI system 100 may include a HOUDINI subsystem 120, which may include program optimization and the application of the concept of steric strain.

In simplified terms, the structure generation process in the HOUDINI subsystem 120 may be viewed as a sequential series of tightly regulated, problem-specific steps whose function is to identify all subset of bonds in an initial hyperstructure that correspond to a complete molecular structure that are compatible with the pool of substructural inferences produced by INTERPRET 104. The initial hyperstructure referred to here (and further described below) is a single entity that represents every possible chemical structure that can be derived from the molecular formula of the compound of unknown structure. It therefore also represents every bond that joins the atoms of the molecular formula together in every one of those possible compounds. If a snapshot could be taken along a pathway leading to a subset of bonds corresponding to a compatible molecular structure (that is, to one solution to the problem), it can be described as a "partial structure". This concept will be invoked later.

The HOUDINI subsystem 120 may be incorporated in the SESAMI system 100 and be based on a concept called convergent structure generation. The HOUDINI subsystem 120 may define an improvement upon an earlier structure generator in SESAMI, COCOA (not shown), which was based on a procedure called structure reduction. The HOUDINI subsystem 120 is more efficient than COCOA and more flexible than COCOA in its input requirements. The replacement of COCOA with the HOUDINI subsystem 120 was seamless as the new program accepts the same output from INTERPRET 104 as the former program.

There are two major components in the HOUDINI subsystem 120. The first takes the output of INTERPRET 104 and produces a new structural representation; a single, integrated substructural network, the constraint network. This has two advantages over the former program approach. First, the information in this single representation can be used far more efficiently in structure generation than a list of separate inferences. Second, the constraint network is richer in information content than the sum of separate inferences.

The second major component of the HOUDINI subsystem 120 is a representation of the problem state. It is a hyperstructure, a two-dimensional, symmetric n×n matrix where n is equal to the number of atoms in the unknown. Rows and columns are labeled with the actual atoms of the unknown. The initial problem state describes all possible bonds between the atoms of the unknown. In its operation, the HOUDINI subsystem 120 maps substructure atoms of the constraint network to the actual atoms of the unknown in the hyperstructure (that is, the matrix). Actually, two processes are at work in concert. At each step, valid structural features are being constructed by changing "possible bonds" to "fixed bonds." At the same time, bonds of the hyperstucture are being deleted by changing other "possible bonds" to "no bonds". The two processes converge in the generation of a valid molecular structure. The matrix has been reduced to a representation of a single molecular structure. The overall process is recursive and continues until all valid structures have been generated.

The HOUDINI subsystem 120 may further include three additional advantageous features that enhance the efficiency of the HOUDINI subsystem 120.

First, the order in which the information contained in the constraint network is used to map substructure atoms in the constraint network to the actual atoms of the unknown in the hyperstructure is controlled by a set of heuristic coefficients in the information manager. That order impacts the efficiency of structure generation. Building a highly efficient structure generator based on the HOUDINI subsystem 120 requires an optimal set of values for the coefficients used by the information manager. However, experience has shown that what is optimal for one structure problem is not necessarily optimal for another problem. If a single set of coefficients is used in all problem-solving cases, some problems are solved efficiently and others are not. Thus, it is necessary to identify an optimal set of coefficients for each problem prior to the start of structure generation. In an initial step, HOUDINI 120 analyzes the problem and selects an optimal set of heuristic coefficients for the particular problem under study. This procedure involves first creating a "signature" for the specific problem. The signature is largely derived from the characteristics of the corresponding constraint network. The signature forms the basis of selecting an optimal set of coefficients.

A second advantageous feature also serves to enhance the efficiency of program execution. As indicated earlier, many of the inferences produced by INTERPRET 104 can consist of two or more alternative substructures. In the HOUDINI subsystem 120 such inferences are processed in concert, not sequentially as in the earlier structure generator COCOA.

In a third advantageous feature, the HOUDINI subsystem 120 employs an additional molecular property to enhance the prospectiveness of the structure generation process: steric strain. Steric strain exists in chemical structures where bonds are forced into abnormal angles resulting in high energies and consequently unstable compounds. In the treatment of naturally occurring compounds in particular, such strained molecules are not usually of interest to the practicing chemist, yet substantial computational time can be expended generating them, compromising program execution and cluttering the output with many structures far too strained for "normal" existence. The current version of the HOUDINI subsystem 120 is endowed with early detection of structural features known to give rise to highly strained molecular structures. This feature can be disabled by the user if highly strained chemical compounds are of interest.

Recall that a snapshot of the structure generation process at some intermediate stage can be described as a partial structure. With the appearance of the first cycle (a closed sequence of n atoms) in a partial structure, strain detection (STRAIN) is initiated. STRAIN continually monitors the expansion of the partial structure, instantly terminating the pathway if a strained feature is detected, thereby eliminating formation of a whole family of highly strained molecular structures containing that feature. STRAIN is guided by a library of strained structural features which extends to polycyclic systems. Although the library of strained structural features detected is not exhaustive, those included generally and dramatically improve computational efficiency.

The planarity of aromatic systems imposes an additional requirement in evaluating strain. The strain knowledge base includes a group of strained features that have at their core a diverse group of planar aromatic systems. Specific features are defined which are applicable to these aromatic core systems. Therefore, as structure generation progresses, where indicated, the HOUDINI subsystem 120 checks for the presence of aromaticity prior to the implementation of STRAIN. In some embodiments of the HOUDINI subsystem 120, cycles of size three to fourteen are tested for aromaticity. In a polycyclic system, all cycles are examined. For example, if a partial structure with the same basic skeletal backbone of phenanthrene is encountered, three six-membered cycles, two ten-membered cycles and one fourteen-membered cycle are each examined for aromatic character. Carbon, nitrogen, oxygen and sulfur can be participating atoms in aromatic systems. The assignment of aromaticity to a cycle requires two conditions to be met: (1) a cycle of m atoms, each capable of sp2 hybridization and contributing one, two or no π electrons (compare aromaticity of pyridine, pyrrole and tropone (cycloheptatrieneone)); and (2) consistency with Hückel's Rule of Aromaticity: in a cycle of m atoms and k π electrons, k=4n+2, where n is an integer of value 1, 2 or 3, and where 2m>k. Thus, naphthalene ($C_{10}H_8$), azulene ($C_{10}H_8$), and [10]annulene ($C_{10}H_{10}$, cyclodecapentaene) are all aromatic compounds with a ten-membered, ten π electron cycle. In the example of a phenanthrene-like skeletal fragment, benzene aromaticity could be identified in any one of the three cycles or in each of the two non-adjacent cycles ("outer cycles"); pnaphthalene aromaticity in either of two adjacent six-membered cycles, or phenanthrene aromaticity if the three cycles are considered collectively.

The steric strain knowledge base in the HOUDINI subsystem 120 can be described in terms of disallowed strained structural features. It should be noted that at the user's discretion, any or all of the features may be disabled in treating a particular structure problem. Where default parameters are included in defining a feature, they too can be changed to better suit the user's needs.

Disallowed Strained Non-Aromatic Strained Features 1.1. Three-membered cycles with one or two exocyclic double bonds.
1.2. Cycles of m $sp^2$ hybridized atoms where m<5. Thus, three and four-membered cycle are disallowed, but the specific three-membered cyclopropenone system is an exception because of its aromatic character and is therefore allowed.
1.3. Cycles of m atoms with an sp hybridized atom, where m<8.
1.4. Bridged [m. n. 0] bicyclic systems where m+n<4. (0 here is zero)
1.5. Bridged [m. n. o] bicyclic systems where atoms m+n+o<5, and where m, n and o>0.
1.6. Bridged [m. n. o] bicyclic systems with a bridgehead double bond, where m+n+o<8, andwherem, n and o>0.
1.7. Bridged [m. n. o] bicyclic systems with two bridgehead double bonds, where m+n+o<9, and where m, n and o>0.

Disallowed Strained Aromatic Features

Steric strain in fragments with an aromatic core can occur in the presence of bridges that severely distort the planarity of the aromatic system. The HOUDINI subsystem identifies all bridges in partial structures with an aromatic core of three to fourteen members, and in each case if the degree of steric strain is excessive that pathway is terminated. Bridge atoms may be any mix of carbon, nitrogen, oxygen and sulfur. In polycyclic systems, a bridge may be confined to a single cycle or cross over two or more cycles. For example, a fragment containing a naphthalene core (a ten-membered, ten π electron aromatic system with an internal bridge) is examined for bridges within each cycle and between the two cycles. Single cycle aromatic systems where the number of atoms is greater than eight are not considered in STRAIN, for example, a partial structure with the ten-membered, ten π electron single cycle [10]annulene core. Such a large cyclic system, although aromatic, is not as rigidly planar as a bridged ten π electron system such as naphthalene.

2.1. Aromatic single n atom cycles where n<9
   2.1.1. An n atom bridge connecting the 1 and 3 positions of an aromatic system of 4 to 8 atoms, where n<5.
   2.1.2. An n atom bridge connecting the 1 and 4 positions of an aromatic system of 6 to 8 atoms, where n<6.
   2.1.3. An n atom bridge connecting the 1 and 5 positions of an aromatic system of 8 atoms, where n<7.
2.2. Aromatic fused two-cycle systems, peripheral cycle size 8-10 with bridges between the two cycles. With the exception of the 1.6 bridge, the following disallowed structural features are applicable to all peripheral cycle sizes. The 1.6 bridge constraint is limited to peripheral cycle size 10. (Earlier rules apply to bridges within the same cycle.)
   2.2.1. An n atom 1, 3 bridge, where n<2
   2.2.2. An n atom 1, 4 bridge, where n<5
   2.2.3. An n atom 1, 5 bridge, where n<7
   2.2.4. An n atom 1, 6 bridge, where n<7

2.3 Aromatic fused three-three cycle systems, peripheral cycle size 14 with bridges between non-adjacent cycles. (Earlier rules apply to bridges within the same cycle and between adjacent cycles.)
   2.3.1. Aromatic compounds with an anthracene core.
      2.3.1.1. An n atom 1, 5 bridge, where n<4
      2.3.1.2. An n atom 1, 6 bridge, where n<6
      2.3.1.3. An n atom 1, 7 bridge, where n<7
      2.3.1.4. An n atom 1, 8 bridge, where n<9
   2.3.2. Aromatic compounds with an phenanthrene core
      2.3.2.1. An n atom 1, 4 bridge, where n<1
      2.3.2.2. An n atom 1, 5 bridge, where n<4
      2.3.2.3. An n atom 1, 6 bridge, where n<6
      2.3.2.4. An n atom 1, 7 bridge, where n<6
      2.3.2.5. An n atom 1, 8 bridge, where n<

Figure 2:
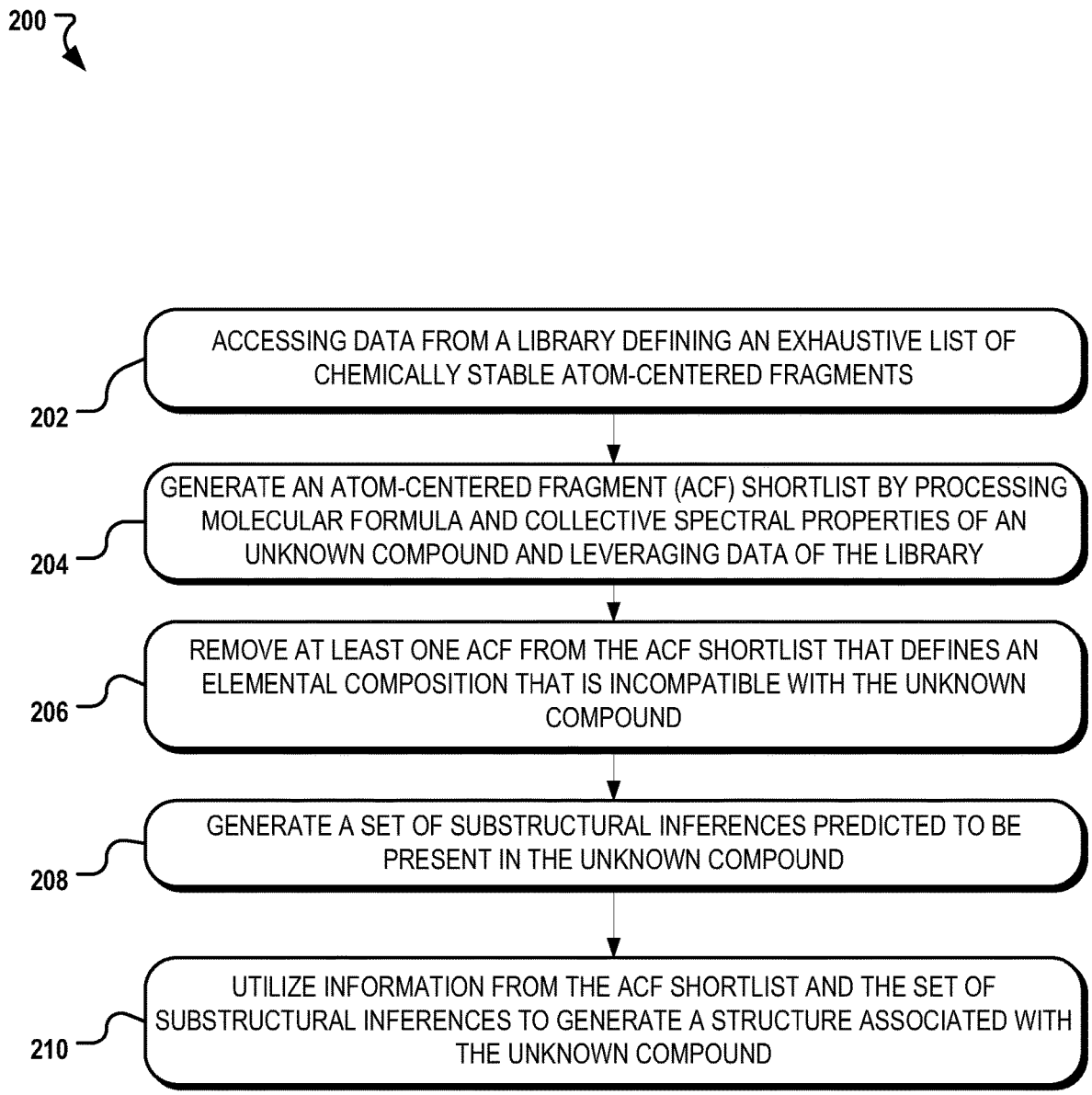
FIG. 2 is a simplified block diagram of a flow chart illustrating possible steps associated with the SESAMI application/system described herein.

Referring to FIG. 2, a process flow 200 related to the aforementioned is indicated. In block 202, data is accessed from the exhaustive library of ACFs 112. In block 204, the ACF shortlist 110 is generated by processing molecular formula and collective spectral properties of an unknown compound and leveraging data of the library. In block 206, at least one ACF is removed from the shortlist that is incompatible with the unknown compound.

In block 208, a set of substructural inferences predicted to be present in the unknown compound is generated. In block 210, information from the ACF shortlist 110 and the set of substructural inferences is utilized to generate a structure associated with the unknown compound.

Other embodiments of the SESAMI system 100 are contemplated. In some embodiments, a diverse set of known, complex compounds derived from natural sources may be used to evaluate aspects of the SESAMI system 100. In some embodiments, two or more constraints are considered in concert rather than individually for evaluating larger and more complex, biologically interesting unknown compounds more reliably and more rapidly. This may involve an example of the whole being greater than the sum of its parts—and minimize structure generation execution times (the "slow step" in problem solving).

In addition, the structure generator of the HOUDINI subsystem 120 may be endowed with a greater ability to examine a particular set of constraints and prioritize their implementation in the structure generation process such that the more restrictive constraints for that particular problem are used more effectively in limiting the search space. (Recall that a structure generation problem can be considered to be a matter of reducing the search space, which represents an enormous number of solutions, to, preferably, one solution or no more than a small number of solutions.)

The information input to the SESAMI system 100 (in addition to the molecular formula of the unknown; most often determined by high-resolution mass spectrometry) is the collective spectroscopic properties of the unknown compound. Some embodiments of the SESAMI system 100 described herein are largely based on hydrogen and carbon nuclear magnetic resonance (NMR) data. This data is processed by the application 102 to infer the structural constraints (also referred to as structural inferences) that serve to limit the search space. These constraints are most often expressed as substructures. Most of these constraints carry a small risk of being invalid, i.e., not actually part of the correctly assigned molecular structure of the unknown.

In some embodiments, the substructures or structures outputted by the application 102 may be incorrect or the information content of the invalid constraint may conflict with information contained in other constraints resulting in no structures being produced. As expected, the larger the number of constraints, the larger the risk of one or more invalid constraints. As such, the SESAMI system 100 may be configured for larger, more complex compounds and to treat a potentially partially-incorrect constraint set in an efficient and automatic fashion.

Figure 3:
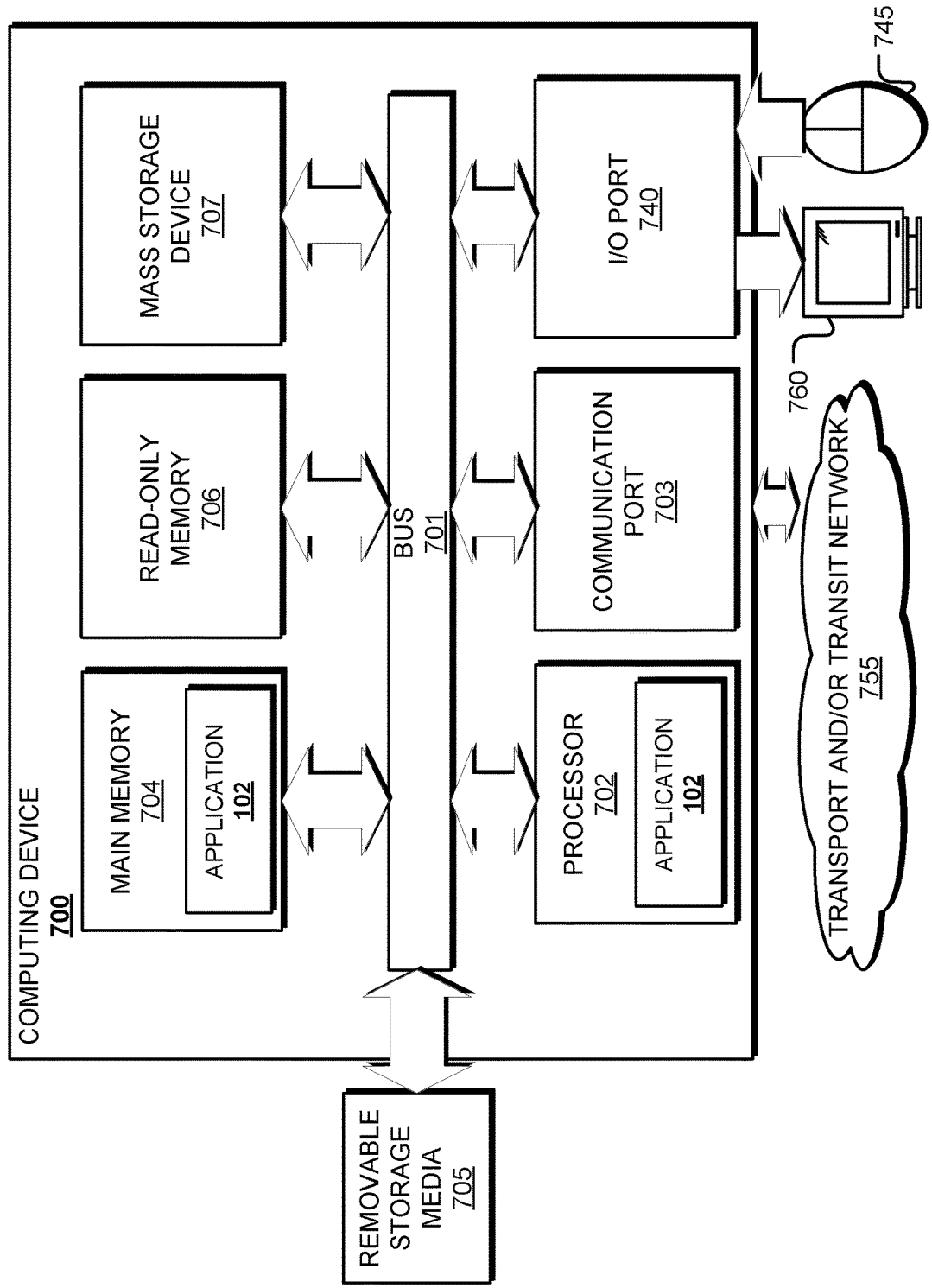
FIG. 3 is a simplified block diagram illustrating a schematic computer diagram for implementing the SESAMI application/system, according to aspects of the present disclosure.

FIG. 3 is an example schematic diagram of a computing device 700 that may implement various methodologies discussed herein. For example, the computing device 700 may execute and store aspects of the application 102 or other aspects of the system 100. The computing device 700 includes a bus 701 (i.e., interconnect), at least one processor 702 or other computing element, at least one communication port 703, a main memory 704, a removable storage media 705, a read-only memory 706, and a mass storage device 707. Processor(s) 702 can be any known processor, such as, but not limited to, an Intel® Itanium® or Itanium 2® processor(s), AMD® Opteron® or Athlon MP® processor(s), or Motorola® lines of processors. Communication port 703 can be any of an RS-232 port for use with a modem based dial-up connection, a 10/100 Ethernet port, a Gigabit port using copper or fiber, or a USB port. Communication port(s) 703 may be chosen depending on a network such as a Local Area Network (LAN), a Wide Area Network (WAN), or any network to which the computer device 700 connects. Computing device may further include a transport and/or transit network 755, a display screen 760, an I/O port 740, and an input device 745 such as a mouse or keyboard.

Main memory 704 can be Random Access Memory (RAM) or any other dynamic storage device(s) commonly known in the art. Read-only memory 706 can be any static storage device(s) such as Programmable Read-Only Memory (PROM) chips for storing static information such as instructions for processor 702. Mass storage device 707 can be used to store information and instructions. For example, hard disks such as the Adaptec® family of Small Computer Serial Interface (SCSI) drives, an optical disc, an array of disks such as Redundant Array of Independent Disks (RAID), such as the Adaptec® family of RAID drives, or any other mass storage devices, may be used.

Bus 701 communicatively couples processor(s) 702 with the other memory, storage, and communications blocks. Bus 701 can be a PCI/PCI-X, SCSI, or Universal Serial Bus (USB) based system bus (or other) depending on the storage devices used. Removable storage media 705 can be any kind of external hard drives, thumb drives, Compact Disc-Read Only Memory (CD-ROM), Compact Disc-Re-Writable (CD-RW), Digital Video Disk-Read Only Memory (DVD-ROM), etc.

Embodiments herein may be provided as a computer program product, which may include a machine-readable medium having stored thereon instructions which may be used to program a computer (or other electronic devices) to perform a process. The machine-readable medium may include, but is not limited to optical discs, CD-ROMs, magneto-optical disks, ROMs, RAMs, erasable programmable read-only memories (EPROMs), electrically erasable programmable read-only memories (EEPROMs), magnetic or optical cards, flash memory, or other type of media/machine-readable medium suitable for storing electronic instructions. Moreover, embodiments herein may also be downloaded as a computer program product, wherein the program may be transferred from a remote computer to a requesting computer by way of data signals embodied in a carrier wave or other propagation medium via a communication link (e.g., modem or network connection).

As shown, main memory 704 may be encoded with the application 204 that supports functionality discussed above. In other words, aspects of the application 102 (and/or other resources as described herein) can be embodied as software code such as data and/or logic instructions (e.g., code stored in the memory or on another computer readable medium such as a disk) that supports processing functionality according to different embodiments described herein. During operation of one embodiment, processor(s) 702 accesses main memory 704 via the use of bus 701 in order to launch, run, execute, interpret, or otherwise perform processes, such as through logic instructions, executing on the processor 702 and based on the application 102 stored in main memory or otherwise tangibly stored.

The description above includes example systems, methods, techniques, instruction sequences, and/or computer program products that embody techniques of the present disclosure. However, it is understood that the described disclosure may be practiced without these specific details. In the present disclosure, the methods disclosed may be implemented as sets of instructions or software readable by a device. Further, it is understood that the specific order or hierarchy of steps in the methods disclosed are instances of example approaches. Based upon design preferences, it is understood that the specific order or hierarchy of steps in the method can be rearranged while remaining within the disclosed subject matter. The accompanying method claims present elements of the various steps in a sample order, and are not necessarily meant to be limited to the specific order or hierarchy presented.

The described disclosure may be provided as a computer program product, or software, that may include a machine-readable medium having stored thereon instructions, which may be used to program a computer system (or other electronic devices) to perform a process according to the present disclosure. A machine-readable medium includes any mechanism for storing information in a form (e.g., software, processing application) readable by a machine (e.g., a computer). The machine-readable medium may include, but is not limited to optical storage medium (e.g., CD-ROM); magneto-optical storage medium, read only memory (ROM); random access memory (RAM); erasable programmable memory (e.g., EPROM and EEPROM); flash memory; or other types of medium suitable for storing electronic instructions.

Certain embodiments are described herein as including one or more subsystems, services, or modules, e.g. modules that execute instructions related to the operation of the application 102, including PRUNE subsystem 108, the INFER subsystem 116, and the like described herein. Such modules may be hardware-implemented, and may thus include at least one tangible unit capable of performing certain operations and may be configured or arranged in a certain manner. For example, a hardware-implemented module may comprise dedicated circuitry that is permanently configured (e.g., as a special-purpose processor, such as a field-programmable gate array (FPGA) or an application-specific integrated circuit (ASIC)) to perform certain operations. A hardware-implemented module may also comprise programmable circuitry (e.g., as encompassed within a general-purpose processor or other programmable processor) that is temporarily configured by software or firmware to perform certain operations. In some example embodiments, one or more computer systems (e.g., a standalone system, a client and/or server computer system, or a peer-to-peer computer system) or one or more processors may be configured by software (e.g., an application or application portion) as a hardware-implemented module that operates to perform certain operations as described herein.

Accordingly, the term "hardware-implemented module" or "module" encompasses a tangible entity, be that an entity that is physically constructed, permanently configured (e.g., hardwired), or temporarily configured (e.g., programmed) to operate in a certain manner and/or to perform certain operations described herein. Considering embodiments in which hardware-implemented modules are temporarily configured (e.g., programmed), each of the hardware-implemented modules need not be configured or instantiated at any one instance in time. For example, where the hardware-implemented modules comprise a general-purpose processor configured using software, the general-purpose processor may be configured as respective different hardware-implemented modules at different times. Software may accordingly configure a processor, for example, to constitute a particular hardware-implemented module at one instance of time and to constitute a different hardware-implemented module at a different instance of time.

Hardware-implemented modules may provide information to, and/or receive information from, other hardware-implemented modules. Accordingly, the described hardware-implemented modules may be regarded as being communicatively coupled. Where multiple of such hardware-implemented modules exist contemporaneously, communications may be achieved through signal transmission (e.g., over appropriate circuits and buses) that connect the hardware-implemented modules. In embodiments in which multiple hardware-implemented modules are configured or instantiated at different times, communications between such hardware-implemented modules may be achieved, for example, through the storage and retrieval of information in memory structures to which the multiple hardware-implemented modules have access. For example, one hardware-implemented module may perform an operation, and may store the output of that operation in a memory device to which it is communicatively coupled. A further hardware-implemented module may then, at a later time, access the memory device to retrieve and process the stored output. Hardware-implemented modules may also initiate communications with input or output devices.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A computer-implemented method, comprising:
utilizing a processor in communication with a tangible storage medium storing instructions that are executed by the processor to perform operations comprising:
conducting spectrum interpretation to generate a set of substructural inferences predicted to be present in a compound of unknown structure, including
generating two separate sets of substructural inferences including a set of uniformly sized, explicitly defined fragments and a set of fragments of any size and degree of ambiguity, and
conducting structure generation, by
utilizing the set of substructural inferences, expressed as substructures, to construct a two-component initial problem state including a hyperstructure representing all possible solutions and a single composite representation of the collective substructural inferences that reveals relationships between the substructural inferences.

2. The computer-implemented method of claim 1, wherein the step of conducting structure generation further comprises:
reducing the initial problem state associated with the compound of unknown structure to one or more complete molecular compounds consistent with the substructural inferences.

3. The computer-implemented method of claim 1, wherein the step of conducting structure generation further comprises:
generating a structure associated with the unknown compound by mapping atoms of the composite representation of the collective substructural inferences to the actual atoms of the hyperstructure in a stepwise, highly regulated process.

4. A computer-implemented method, comprising:
utilizing a processor in communication with a tangible storage medium storing instructions that are executed by the processor to perform operations comprising:
conducting spectrum interpretation to generate a set of substructural inferences predicted to be present in a compound of unknown structure, and
conducting structure generation, by
utilizing the set of substructural inferences, expressed as substructures, to construct a two-component initial problem state including a hyperstructure representing all possible solutions and a single composite representation of the collective substructural inferences that reveals relationships between the substructural inferences, wherein the step of conducting structure generation further comprises:
reducing the initial problem state associated with the compound of unknown structure to one or more complete molecular compounds consistent with the substructural inferences.

5. The computer-implemented method of claim 4, further comprising generating two separate sets of substructural inferences including a set of uniformly sized, explicitly defined fragments and a set of fragments of any size and degree of ambiguity.

6. A computer-implemented method, comprising:
utilizing a processor in communication with a tangible storage medium storing instructions that are executed by the processor to perform operations comprising:
conducting spectrum interpretation to generate a set of substructural inferences predicted to be present in a compound of unknown structure, and
conducting structure generation, by
utilizing the set of substructural inferences, expressed as substructures, to construct a two-component initial problem state including a hyperstructure representing all possible solutions and a single composite representation of the collective substructural inferences that reveals relationships between the substructural inferences, and
generating a structure associated with the unknown compound by mapping atoms of the composite representation of the collective substructural inferences to the actual atoms of the hyperstructure in a stepwise, highly regulated process.

7. The computer-implemented method of claim 6, further comprising generating two separate sets of substructural inferences including a set of uniformly sized, explicitly defined fragments and a set of fragments of any size and degree of ambiguity.

* * * * *